US011259999B2

(12) United States Patent
Ning et al.

(10) Patent No.: US 11,259,999 B2
(45) Date of Patent: Mar. 1, 2022

(54) METHOD FOR MAKING TOOTHPASTE ENABLING ENAMEL RESTORATION

(71) Applicants: Yunnan Baiyao Group Health Product Co., Ltd., Yunnan (CN); Xi'an University of Science and Technology, Shaanxi (CN)

(72) Inventors: Kegong Ning, Yunnan (CN); Yongjun He, Shaanxi (CN)

(*) Notice: Subject to any disclaimer, the term of this patent is extended or adjusted under 35 U.S.C. 154(b) by 0 days.

(21) Appl. No.: 17/120,862

(22) Filed: Dec. 14, 2020

(65) Prior Publication Data
US 2021/0251858 A1 Aug. 19, 2021

(30) Foreign Application Priority Data
Feb. 13, 2020 (CN) .......................... 202010089806.8

(51) Int. Cl.
| *A61K 8/06* | (2006.01) |
| *A61K 8/24* | (2006.01) |
| *A61K 8/37* | (2006.01) |
| *A61K 8/92* | (2006.01) |
| *A61Q 11/00* | (2006.01) |
| *B01F 3/08* | (2006.01) |

(52) U.S. Cl.
CPC ............... *A61K 8/066* (2013.01); *A61K 8/24* (2013.01); *A61K 8/375* (2013.01); *A61K 8/92* (2013.01); *A61Q 11/00* (2013.01); *B01F 3/0807* (2013.01); *B01F 3/088* (2013.01); *A61K 2800/5922* (2013.01); *A61K 2800/805* (2013.01); *B01F 2003/0838* (2013.01); *B01F 2003/0884* (2013.01)

(58) Field of Classification Search
CPC ... A61K 8/02; A61K 8/19; A61K 8/31; A61K 8/92; A61Q 11/00
USPC ............................................ 424/49, 57, 602
See application file for complete search history.

(56) References Cited

U.S. PATENT DOCUMENTS

2014/0105941 A1* 4/2014 Mchale .................. A61K 9/006
424/401

OTHER PUBLICATIONS

Saeidy et al., "Microencapsultion of Calcium Using Water-in-Oil-in-Water." Journal of Dispersion Science and Technology vol. 35, issue 3; published Mar. 12, 2014 (Year: 2014).*

* cited by examiner

*Primary Examiner* — Walter E Webb
(74) *Attorney, Agent, or Firm* — Lambert Shortell & Connaughton; David J. Connaughton, Jr.; Justin P. Tinger

(57) ABSTRACT

A method for making a toothpaste enabling enamel restoration proposes to encapsulate soluble calcium and phosphate salts within corresponding internal water phases in respective water-in-oil-in-water emulsions. In this way, the soluble calcium and phosphate salts can be present stably in the toothpaste over a long period of time without causing precipitation of calcium phosphate. When the toothpaste of the present disclosure is used in brushing teeth, the water-in-oil-in-water emulsions are ruptured under the effect of friction and pressing, releasing the soluble calcium and/or phosphate salts encapsulated within the corresponding internal water phases. As a result, the liquid in the user's oral cavity will contain high concentrations of calcium and phosphate ions, which can enhance the rate of remineralization of enamel and/or dentin exposed to the oral cavity.

5 Claims, No Drawings

METHOD FOR MAKING TOOTHPASTE ENABLING ENAMEL RESTORATION

TECHNICAL FIELD

The present disclosure is generally related to the medical field or the field of household chemicals, and in particular to biomimetic mineralization or remineralization (restoration) of dentin and/or enamel in a tooth structure, more particularly to a method for making a toothpaste enabling enamel restoration.

BACKGROUND

Enamel is the hardest tissue in the human body. As the outer covering of the tooth, the enamel is always subject to physical attacks including occlusion, friction and wear, and to chemical attacks such as corrosion caused by acids that are produced by food or bacteria. In the case that the pH of the mouth is less than 5.5, hydroxyapatite, the major mineral component of the enamel, may dissolve, causing demineralization of the enamel.

Calcium and phosphate ions present in the saliva can buffer the variation of the pH value of the saliva to some extent, inhibiting the dissolution of hydroxyapatite. In the case that the saliva has a pH value greater than 5.5 and contains high concentrations of calcium and phosphate ions, calcium phosphate would be produced for tooth remineralization. However, typically, the concentrations of the calcium and phosphate ions are too low in the saliva to produce sufficient amount of hydroxyapatite to restore demineralized enamel.

Calcium and phosphate salts contained in the toothpaste can lead to increased concentrations of calcium and phosphate ions in the oral environment during brushing of teeth, which can promote the remineralization of the teeth. However, if the calcium and phosphate salts contained in a toothpaste have a low solubility, the toothpaste may provide the oral environment with low concentrations of calcium and phosphate ions in use. If the calcium and phosphate salts contained in a toothpaste have a high solubility, the calcium ions and the phosphate ions in the toothpaste may react rapidly with each other to form a precipitate due to the fact that octacalcium phosphate, calcium phosphate, dicalcium phosphate, hydroxyapatite and the like have a low solubility product. Thus, in this case, the toothpaste will still have low concentrations of free calcium and phosphate ions. Accordingly, adding calcium and phosphate salts to a toothpaste base directly can only provide low concentrations of free calcium and phosphate ions, which may lead to a low rate of enamel remineralization during limited tooth brushing time and at limited tooth brushing frequency.

SUMMARY

An objective of the present disclosure is to provide a method for making a toothpaste which can enable the liquid in a user's oral cavity to have high concentrations of calcium and phosphate ions when being used in brushing teeth and thus enable an increased rate of enamel remineralization, thereby promoting enamel restoration.

Accordingly, the objective of the present disclosure is realized by a method for making a toothpaste, comprising:
(1) preparation of a water-in-oil-in-water emulsion containing a soluble calcium salt, the preparation of the emulsion comprising:

adding a surfactant suitable for medical and oral care to a nonpolar substance suitable for oral care and mixing with stirring at 0 to 80° C. until homogeneous to form an oil phase, wherein, a mass ratio of the surfactant to the nonpolar substance is from 0.02:100 to 5:100;

adding to water a substance capable of supplying free calcium ions to form an aqueous solution with a calcium ion concentration of 0.1 to 60%;

mixing the aqueous solution with the oil phase at a volume ratio of 0.5:9.5 to 1.5:0.5, followed by stirring with a high-speed disperser at a stirring speed of 10 to 54,000 rpm and at 0 to 80° C. for 0.5 to 120 minutes to form a water-in-oil emulsion;

adding to water a surfactant suitable for medical and oral care to form a water phase, wherein, a mass ratio of the surfactant to the water is from 0.01:100 to 5:100; and mixing the water-in-oil emulsion with the water phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil-in-water emulsion containing a soluble calcium salt;

(2) preparation of a water-in-oil-in-water emulsion containing a soluble phosphate salt, the preparation of the emulsion comprising:

adding a surfactant suitable for medical and oral care to a natural vegetable oil and mixing with stirring at 2 to 80° C. until homogeneous to form an oil phase, wherein, a mass ratio of the surfactant to the vegetable oil is from 0.02:100 to 5:100;

adding to water a substance capable of supplying free phosphate, hydrogen phosphate, and/or dihydrogen phosphate ions to form an aqueous solution, with a concentration of the phosphate, hydrogen phosphate, and/or dihydrogen phosphate ions being 0.1 to 60%;

mixing the aqueous solution with the oil phase at a volume ratio of 0.5:9.5 to 1.5:0.5, followed by stirring with a high-speed disperser at a stirring speed of 300 to 24,000 rpm and at 10 to 80° C. for 10 seconds to 120 minutes to form a water-in-oil emulsion;

adding to water a surfactant suitable for medical and oral care to form a water phase, wherein, a mass ratio of the surfactant to the water is from 0.02:100 to 5:100; and mixing the water-in-oil emulsion with the water phase at a volume ratio of 0.5:9.5 to 1.5:0.5, followed by stirring with a high-speed disperser at a stirring speed of 300 to 24,000 rpm and at 10 to 80° C. for 10 seconds to 120 minutes to form a water-in-oil-in-water emulsion containing a soluble phosphate salt;

(3) preparation of a toothpaste containing both a soluble calcium salt and a soluble phosphate salt, the preparation of the toothpaste comprising:

mixing the water-in-oil-in-water emulsion containing a soluble calcium salt and the water-in-oil-in-water emulsion containing a soluble phosphate salt with a toothpaste base with a stirring speed of 300 to 24,000 rpm at 10 to 80° C. for 10 seconds to 120 minutes to obtain a toothpaste containing both a soluble calcium salt and a soluble phosphate salt, wherein, a molar ratio of the calcium ions in the water-in-oil-in-water emulsion containing a soluble calcium salt to the phosphate ions in the water-in-oil-in-water emulsion containing a soluble phosphate salt is 5:3, and the ratio of the mass of the water-in-oil-in-water emulsion containing a soluble calcium salt and the water-in-oil-in-water emulsion containing a soluble phosphate salt to mass of the toothpaste base is from 1:19 to 19:1.

The surfactant suitable for medical and oral care used in the steps (1) and (2) may be one or more of sucrose fatty acid ester, Span 60, Span 65, glyceryl stearate, sorbitan monostearate, sorbitan monopalmitate, sodium stearoyl lactylate, calcium stearoyl lactylate, glycerol ester of rosin, sucrose acetate, sucrose acetate isobutyrate, Span 80, polyoxyethylene anhydroxylitol monostearate, hydrogenated rosin glycerin ester, diacetyl tartaric acid esters of mono or diglycerides, propylene glycol fatty acid ester, dimeric glycerine monostearate, monoacylglyceride, trimeric glyceride, propylene glycol fatty acid ester, granulesten, sodium lauryl sulfate, a glucoside nonionic surfactant, polyoxyethylene hydrogenated castor oil (a nonionic surfactant), sodium lauroyl sarcosinate, sodium lauroyl glutamate, and glycerol monolaurate.

The nonpolar substance suitable for oral care used in the steps (1) and (2) may be a natural vegetable oil selected from one or more of rapeseed oil, peanut oil, cannabis oil, corn oil, olive oil, camellia oil, palm oil, sunflower oil, soybean oil, sesame oil, linseed oil, grape seed oil, walnut oil, peony seed oil, and coconut oil, an animal fat or oil selected from one or more of lard oil, beef fat, mutton fat, chicken oil, snake oil, oviductus ranae, and fish oil, or a synthetic oil that is a nonpolar oil produced from petroleum, natural gas or coal and nontoxic to the human body.

The substance capable of supplying free calcium ions may be one or more of calcium chloride, calcium nitrate, calcium gluconate, calcium bicarbonate, calcium bisulfate, and calcium lactate.

The substance capable of supplying free phosphate, hydrogen phosphate, and/or dihydrogen phosphate ions may be one or more of potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate.

The method of the present disclosure provides several advantages over the prior art.

The present disclosure proposes to encapsulate the soluble calcium and phosphate salts within corresponding internal water phases in respective water-in-oil-in-water emulsions. In this way, the calcium and phosphate salts can be present stably in the toothpaste over a long period of time without causing precipitation of calcium phosphate. When the toothpaste of the present disclosure is used in brushing teeth, the water-in-oil-in-water emulsions are ruptured under the effect of friction, releasing the soluble calcium and/or phosphate salts encapsulated within the corresponding internal water phases. As a result, the liquid in the user's oral cavity will contain high concentrations of calcium and phosphate ions, which can enhance the rate of remineralization of enamel and/or dentin exposed to the oral cavity.

DETAILED DESCRIPTION

Embodiments of the present disclosure will now be further described by way of examples.

Example 1

(1) Preparation of a Water-in-Oil-in-Water Emulsion Containing a Soluble Calcium Salt 0.02 g of sucrose fatty acid ester was added to 100 g of rapeseed oil and mixed with stirring while heating until homogeneous to form an oil phase. During this, the mixture was heated to 30° C. Thereafter, 0.5 ml of a 0.1 wt. % calcium chloride solution and 9.5 ml of the rapeseed oil containing the sucrose fatty acid ester were mixed with a high-speed disperser at a stirring speed of 300 rpm and at 80° C. for 120 minutes to obtain a water-in-oil emulsion.

5 g of sodium lauryl sulfate was added to 100 g of water to form a water phase. 0.5 ml of the water-in-oil emulsion obtained above and 9.5 ml of the water phase were mixed with a high-speed disperser at a stirring speed of 24,000 rpm and at 30° C. for 0.5 minutes to obtain a water-in-oil-in-water emulsion containing a soluble calcium salt.

(2) Preparation of a Water-in-Oil-in-Water Emulsion Containing a Soluble Phosphate Salt 5 g of sucrose fatty acid ester was added to 100 g of rapeseed oil and mixed with stirring while heating until homogeneous to form an oil phase. During this, the mixture was heated to 80° C. Thereafter, 0.5 ml of a 0.1 wt. % potassium phosphate solution and 9.5 ml of the rapeseed oil containing the silicon dioxide were mixed with a high-speed disperser at a stirring speed of 300 rpm and at 30° C. for 120 minutes to obtain a water-in-oil emulsion.

0.02 g of sodium lauryl sulfate was added to 100 g of water to form a water phase. 0.5 ml of the water-in-oil emulsion obtained above and 9.5 ml of the water phase were mixed with a high-speed disperser at a stirring speed of 24,000 rpm and at 80° C. for 0.5 minutes to obtain a water-in-oil-in-water emulsion containing a soluble phosphate salt.

(3) Preparation of a Toothpaste Containing Both a Soluble Calcium Slat and a Soluble Phosphate Salt 0.5 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 3:2) and 9.5 g of a toothpaste base were mixed with a high-speed disperser at a stirring speed of 24,000 rpm and at 30° C. for 0.5 minutes to produce a toothpaste product.

Tests showed that a rate of enamel remineralization provided by the toothpaste in this Example was 23 times that provided by the conventional toothpaste containing hydroxyapatite.

Example 2

Toothpastes were prepared in the same manner as in Example 1 except that: —the surfactant used in preparation of the water-in-oil emulsion was one of: Span 60, Span 65, glyceryl stearate, sorbitan monostearate, sorbitan monopalmitate, sodium stearoyl lactylate, calcium stearoyl lactylate, glycerol ester of rosin, sucrose acetate, sucrose acetate isobutyrate, Span 80, polyoxyethylene anhydroxylitol monostearate, hydrogenated rosin glycerin ester, diacetyl tartaric acid esters of mono or diglycerides, propylene glycol fatty acid ester, dimeric glycerine monostearate, monoacylglyceride, trimeric glyceride, propylene glycol fatty acid ester, granulesten, and glycerol monolaurate, or at least two of: sucrose fatty acid ester, Span 60, Span 65, glyceryl stearate, sorbitan monostearate, sorbitan monopalmitate, sodium stearoyl lactylate, calcium stearoyl lactylate, glycerol ester of rosin, sucrose acetate, sucrose acetate isobutyrate, Span 80, polyoxyethylene anhydroxylitol monostearate, hydrogenated rosin glycerin ester, diacetyl tartaric acid esters of mono or diglycerides, propylene glycol fatty acid ester, dimeric glycerine monostearate, monoacylglyceride, trimeric glyceride, propylene glycol fatty acid ester, granulesten, and glycerol monolaurate (other than the surfactant used in Example 1); —the surfactant used in preparation of the oil-in-water emulsion was one of: sodium caseinate, sesbania gum, Tween 60, Tween 80, and sodium lauryl sulfate, or at least two of: sodium lauryl sulfate, sodium caseinate, sesbania gum, Tween 60, Tween 80, and sodium lauryl sulfate; —the soluble calcium salt used was one of: calcium gluconate, calcium bicarbonate, calcium bisulfate, and calcium lactate, or at least two of: calcium nitrate, calcium gluconate, calcium bicarbonate, calcium bisulfate, and calcium lactate; —the soluble phosphate salt used was one of: sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate, or at least two of: potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate; —and the edible oil used was one of: peanut oil, cannabis oil, corn oil, olive oil, camellia oil, palm oil, sunflower oil, soybean oil, sesame oil, linseed oil, grape seed oil, walnut oil, peony seed oil, and coconut oil, or at least two of: rapeseed oil, peanut oil, cannabis oil, corn oil, olive oil, camellia oil, palm oil, sunflower oil, soybean oil, sesame oil, linseed oil, grape seed oil, walnut oil, peony seed oil, and coconut oil.

Tests showed that a rate of enamel remineralization provided by the toothpastes in this Example was 5 or more times that provided by the conventional toothpaste containing hydroxyapatite.

Example 3

(1) Preparation of a Water-in-Oil-in-Water Emulsion Containing a Soluble Calcium Salt 0.1 g of glyceryl stearate was added to 2 g of sunflower oil and mixed with stirring while heating until homogeneous to form an oil phase. During this, the mixture was heated to 80° C. Thereafter, 1.5 ml of a 60 wt. % calcium nitrate solution and 1 ml of the sunflower oil containing the glyceryl stearate were mixed with a high-speed disperser at a stirring speed of 24,000 rpm and at 30° C. for 0.5 minutes to obtain a water-in-oil emulsion.

1 g of sodium caseinate was added to 4 g of water and stirred until homogeneous to form a water phase. 1.5 ml of the water-in-oil emulsion obtained above and 1 ml of the water phase were mixed with a high-speed disperser at a stirring speed of 300 rpm and at 80° C. for 120 minutes to obtain a water-in-oil-in-water emulsion containing calcium ions.

(2) Preparation of a Water-in-Oil-in-Water Emulsion Containing a Soluble Phosphate Salt 0.5 g of glyceryl stearate was added to 2 g of sunflower oil and mixed with stirring while heating until homogeneous to form an oil phase. During this, the mixture was heated to 30° C. Thereafter, 1.5 ml of a 60 wt. % potassium dihydrogen phosphate solution and 1 ml of the sunflower oil containing the glyceryl stearate were mixed with a high-speed disperser at a stirring speed of 24,000 rpm and at 80° C. for 0.5 minutes to obtain a water-in-oil emulsion.

1 g of sodium caseinate was added to 4 g of water and stirred until homogeneous to form a water phase. 1.5 ml of the water-in-oil emulsion obtained above and 1 ml of the water phase were mixed with a high-speed disperser at a stirring speed of 300 rpm and at 30° C. for 120 minutes to obtain a water-in-oil-in-water emulsion containing phosphate ions.

(3) Preparation of a Toothpaste Containing Both a Soluble Calcium Slat and a Soluble Phosphate Salt 4 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being any ratio) and 0.2 g of a toothpaste base were mixed with a high-speed disperser at a stirring speed of 300 rpm and at 80° C. for 120 minutes to produce a toothpaste product containing both a soluble calcium slat and a soluble phosphate salt.

Tests showed that a rate of enamel remineralization provided by the toothpaste in this Example was 2.8 or more times that provided by the conventional toothpaste containing hydroxyapatite.

Example 4

Toothpastes were prepared in the same manner as in Example 3 except that: —the surfactant used in preparation of the water-in-oil emulsion was one of: sucrose fatty acid ester, Span 60, Span 65, sorbitan monostearate, sorbitan monopalmitate, sodium stearoyl lactylate, calcium stearoyl lactylate, glycerol ester of rosin, sucrose acetate, sucrose acetate isobutyrate, Span 80, polyoxyethylene anhydroxylitol monostearate, hydrogenated rosin glycerin ester, diacetyl tartaric acid esters of mono or diglycerides, propylene glycol fatty acid ester, dimeric glycerine monostearate, monoacylglyceride, trimeric glyceride, propylene glycol fatty acid ester, granulesten, and glycerol monolaurate, or at least two of: sucrose fatty acid ester, Span 60, Span 65, glyceryl stearate, sorbitan monostearate, sorbitan monopalmitate, sodium stearoyl lactylate, calcium stearoyl lactylate, glycerol ester of rosin, sucrose acetate, sucrose acetate isobutyrate, Span 80, polyoxyethylene anhydroxylitol monostearate, hydrogenated rosin glycerin ester, diacetyl tartaric acid esters of mono or diglycerides, propylene glycol fatty acid ester, dimeric glycerine monostearate, monoacylglyceride, trimeric glyceride, propylene glycol fatty acid ester, granulesten, and glycerol monolaurate (other than the surfactant used in Example 3); —the surfactant used in preparation of the oil-in-water emulsion was one of: sodium lauryl sulfate, sesbania gum, Tween 60, Tween 80, and sodium lauryl sulfate, or at least two of: sodium lauryl sulfate, sodium caseinate, sesbania gum, Tween 60, Tween 80, and sodium lauryl sulfate; —the soluble calcium salt used was one of: calcium chloride, calcium gluconate, calcium bicarbonate, calcium bisulfate, and calcium lactate, or at least two of: calcium chloride, calcium nitrate, calcium gluconate, calcium bicarbonate, calcium bisulfate, and calcium lactate; —the soluble phosphate salt used was one of: potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate, or at least two of: potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate; —and the edible oil used was one of:

rapeseed oil, peanut oil, cannabis oil, corn oil, olive oil, camellia oil, palm oil, soybean oil, sesame oil, linseed oil, grape seed oil, walnut oil, peony seed oil, and coconut oil, or at least two of: rapeseed oil, peanut oil, cannabis oil, corn oil, olive oil, camellia oil, palm oil, sunflower oil, soybean oil, sesame oil, linseed oil, grape seed oil, walnut oil, peony seed oil, and coconut oil.

Tests showed that a rate of enamel remineralization provided by the toothpastes in this Example was 3.7 or more times that provided by the conventional toothpaste containing hydroxyapatite.

Example 5

(1) Preparation of a Water-in-Oil-in-Water Emulsion Containing a Soluble Calcium Salt 0.5 g of glycerol ester of rosin was added to 50 g of olive oil and mixed with stirring while heating until homogeneous to form an oil phase. During this, the mixture was heated to 30° C. Thereafter, 2.5 ml of a 2 wt. % calcium gluconate solution and 7.5 ml of the olive oil containing the glycerol ester of rosin were mixed with a high-speed disperser at a stirring speed of 6,000 rpm and at 30° C. for 40 minutes to obtain a water-in-oil emulsion.

0.8 g of sodium lauryl sulfate was added to 25 g of water and stirred while heating until homogeneous to form a water phase. During this, the mixture was heated to 30° C. 3 ml of the water-in-oil emulsion obtained above and 2 ml of the water phase were mixed with a high-speed disperser at a stirring speed of 4,000 rpm and at 30° C. for 20 minutes to obtain a water-in-oil-in-water emulsion containing calcium ions.

(2) Preparation of a Water-in-Oil-in-Water Emulsion Containing a Soluble Phosphate Salt 0.1 g of trimeric glyceride was added to 10 g of peanut oil and mixed with stirring while heating until homogeneous to form an oil phase. During this, the mixture was heated to 30° C. Thereafter, 2 ml of a 5.5 wt. % sodium hydrogen phosphate solution and 5 ml of the peanut oil containing the trimeric glyceride were mixed with a high-speed disperser at a stirring speed of 18,000 rpm and at 30° C. for 10 minutes to obtain a water-in-oil emulsion.

0.3 g of sodium lauryl sulfate was added to 10 g of water to form a water phase. 3 ml of the water-in-oil emulsion obtained above and 5 ml of the water phase were mixed with a high-speed disperser at a stirring speed of 5,000 rpm and at 30° C. for 40 minutes to obtain a water-in-oil-in-water emulsion containing phosphate ions.

(3) Preparation of a Toothpaste Containing Both a Soluble Calcium Slat and a Soluble Phosphate Salt 3 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 3:2) and 3 g of a toothpaste base were mixed with a high-speed disperser at a stirring speed of 9,000 rpm and at 30° C. for 15 minutes to produce a toothpaste product.

Tests showed that a rate of enamel remineralization provided by the toothpaste in this Example was 2.1 times that provided by the conventional toothpaste containing hydroxyapatite.

Example 6

(1) Preparation of a Water-in-Oil-in-Water Emulsion Containing a Soluble Calcium Salt 0.5 g of sodium stearoyl lactylate was added to coconut oil and mixed with stirring while heating until homogeneous to form an oil phase. During this, the mixture was heated to 30° C. Thereafter, 3.5 ml of a 5 wt. % calcium bicarbonate solution and 3.5 ml of the olive oil containing the sodium stearoyl lactylate were mixed with a high-speed disperser at a stirring speed of 7,500 rpm and at 30° C. for 15 minutes to obtain a water-in-oil emulsion.

2 g of sodium lauryl sulfate was added to 50 g of water to form a water phase. 2 ml of the water-in-oil emulsion obtained above and 2 ml of the water phase were mixed with a high-speed disperser at a stirring speed of 15,000 rpm and at 30° C. for 20 minutes to obtain a water-in-oil-in-water emulsion containing calcium ions.

(2) Preparation of a Water-in-Oil-in-Water Emulsion Containing a Soluble Phosphate Salt 0.5 g of granulesten was added to 10 g of soybean oil and mixed with stirring while heating until homogeneous to form an oil phase. During this, the mixture was heated to 30° C. Thereafter, 1 ml of a 3.6 wt. % ammonium hydrogen phosphate solution and 4 ml of the soybean oil containing the granulesten were mixed with a high-speed disperser at a stirring speed of 1,200 rpm and at 30° C. for 70 minutes to obtain a water-in-oil emulsion.

0.8 g of sodium lauryl sulfate was added to 20 g of water and stirred until homogeneous to form a water phase. 1.5 ml of the water-in-oil emulsion obtained above and 1 ml of the water phase were mixed with a high-speed disperser at a stirring speed of 12,000 rpm and at 30° C. for 45 minutes to obtain a water-in-oil-in-water emulsion containing phosphate ions.

(3) Preparation of a Toothpaste Containing Both a Soluble Calcium Slat and a Soluble Phosphate Salt 3 g of the water-in-oil-in-water emulsion containing a soluble calcium salt obtained in the step (1) and the water-in-oil-in-water emulsion containing a soluble phosphate salt obtained in the step (2) (with the molar ratio of the calcium ions in the water-in-oil-in-water emulsion containing a soluble calcium salt to the phosphate ions in the water-in-oil-in-water emulsion containing a soluble phosphate salt being 3:2) and 2 g of a toothpaste base were mixed with a high-speed disperser at a stirring speed of 8,000 rpm and at 30° C. for 35 minutes to produce a toothpaste product.

Tests showed that a rate of enamel remineralization provided by the toothpaste in this Example was 2.3 or more times that provided by the conventional toothpaste containing hydroxyapatite.

The above description is merely preferred embodiments of the present disclosure and not intended to limit the scope of the present disclosure. Any simple modifications, changes, and equivalent structures that are based on the principle and concept of the present disclosure shall all be within the scope of the present disclosure.

What is claimed is:

1. A method for making a toothpaste enabling enamel restoration, comprising steps of:
  (1) preparation of a water-in-oil-in-water emulsion containing a soluble calcium salt, the preparation of the emulsion comprising:
    adding a surfactant suitable for medical and oral care to a nonpolar substance suitable for oral care and mixing with stirring at 0 to 80° C. until homogeneous to form an oil phase, wherein, a mass ratio of the surfactant to the nonpolar substance is from 0.02:100 to 5:100;

adding to water a substance capable of supplying free calcium ions to form an aqueous solution with a calcium ion concentration of 0.1 to 60%;

mixing the aqueous solution with the oil phase at a volume ratio of 0.5:9.5 to 1.5:0.5, followed by stirring with a high-speed disperser at a stirring speed of 10 to 54,000 rpm and at 0 to 80° C. for 0.5 to 120 minutes to form a water-in-oil emulsion;

adding to water a surfactant suitable for medical and oral care to form a water phase, wherein, a mass ratio of the surfactant to the water is from 0.01:100 to 5:100; and mixing the water-in-oil emulsion with the water phase at a volume ratio of 0.5:9.5 to 1.5:0.5, followed by stirring with a high-speed disperser at a stirring speed of 10 to 24,000 rpm and at 30 to 80° C. for 0.5 to 120 minutes to form a water-in-oil-in-water emulsion containing a soluble calcium salt;

(2) preparation of a water-in-oil-in-water emulsion containing a soluble phosphate salt, the preparation of the emulsion comprising:

adding a surfactant suitable for medical and oral care to a natural vegetable oil and mixing with stirring at 2 to 80° C. until homogeneous to form an oil phase, wherein, a mass ratio of the surfactant to the vegetable oil is from 0.02:100 to 5:100;

adding to water a substance capable of supplying free phosphate, hydrogen phosphate, and/or dihydrogen phosphate ions to form an aqueous solution, with a concentration of the phosphate, hydrogen phosphate, and/or dihydrogen phosphate ions being 0.1 to 60%;

mixing the aqueous solution with the oil phase at a volume ratio of 0.5:9.5 to 1.5:0.5, followed by stirring with a high-speed disperser at a stirring speed of 300 to 24,000 rpm and at 10 to 80° C. for 10 seconds to 120 minutes to form a water-in-oil emulsion;

adding to water a surfactant suitable for medical and oral care to form a water phase, wherein, a mass ratio of the surfactant to the water is from 0.02:100 to 5:100; and mixing the water-in-oil emulsion with the water phase at a volume ratio of 0.5:9.5 to 1.5:0.5, followed by stirring with a high-speed disperser at a stirring speed of 300 to 24,000 rpm and at 10 to 80° C. for 10 seconds to 120 minutes to form a water-in-oil-in-water emulsion containing a soluble phosphate salt; and (3) preparation of a toothpaste containing both a soluble calcium salt and a soluble phosphate salt, the preparation of the toothpaste comprising:

mixing the water-in-oil-in-water emulsion containing a soluble calcium salt and the water-in-oil-in-water emulsion containing a soluble phosphate salt with a toothpaste base with a stirring speed of 300 to 24,000 rpm at 10 to 80° C. for 10 seconds to 120 minutes to obtain a toothpaste containing both a soluble calcium salt and a soluble phosphate salt, wherein, a molar ratio of the calcium ions in the water-in-oil-in-water emulsion containing a soluble calcium salt to the phosphate ions in the water-in-oil-in-water emulsion containing a soluble phosphate salt is 5:3, and the ratio of the mass of the water-in-oil-in-water emulsion containing a soluble calcium salt and the water-in-oil-in-water emulsion containing a soluble phosphate salt to mass of the toothpaste base is from 1:19 to 19:1.

2. The method according to claim 1, wherein, the surfactant suitable for medical and oral care used in the steps (1) and (2) is one or more of sucrose fatty acid ester, Span 60, Span 65, glyceryl stearate, sorbitan monostearate, sorbitan monopalmitate, sodium stearoyl lactylate, calcium stearoyl lactylate, glycerol ester of rosin, sucrose acetate, sucrose acetate isobutyrate, Span 80, polyoxyethylene anhydroxylitol monostearate, hydrogenated rosin glycerin ester, diacetyl tartaric acid esters of mono or diglycerides, propylene glycol fatty acid ester, dimeric glycerine monostearate, monoacylglyceride, trimeric glyceride, propylene glycol fatty acid ester, granulesten, sodium lauryl sulfate, glucoside nonionic surfactants, polyoxyethylene hydrogenated castor oil (a nonionic surfactant), sodium lauroyl sarcosinate, sodium lauroyl glutamate, and glycerol monolaurate.

3. The method according to claim 1, wherein, the nonpolar substance suitable for oral care used in the steps (1) and (2) is a natural vegetable oil selected from one or more of rapeseed oil, peanut oil, cannabis oil, corn oil, olive oil, camellia oil, palm oil, sunflower oil, soybean oil, sesame oil, linseed oil, grape seed oil, walnut oil, peony seed oil, and coconut oil, an animal fat or oil selected from one or more of lard oil, beef fat, mutton fat, chicken oil, snake oil, oviductus ranae, and fish oil, or a synthetic oil that is a nonpolar oil produced from petroleum, natural gas or coal and nontoxic to the human body.

4. The method according to claim 1, wherein, the substance capable of supplying free calcium ions is one or more of calcium chloride, calcium nitrate, calcium gluconate, calcium bicarbonate, calcium bisulfate, and calcium lactate.

5. The method according to claim 1, wherein, the substance capable of supplying free phosphate, hydrogen phosphate, and/or dihydrogen phosphate ions is one or more of potassium phosphate, sodium phosphate, ammonium phosphate, potassium hydrogen phosphate, sodium hydrogen phosphate, ammonium hydrogen phosphate, potassium dihydrogen phosphate, sodium dihydrogen phosphate, and ammonium dihydrogen phosphate.

* * * * *